United States Patent
Wurn et al.

(10) Patent No.: US 8,497,303 B2
(45) Date of Patent: Jul. 30, 2013

(54) METHOD TO ENHANCE AQUEOUS SOLUBILITY OF POORLY SOLUBLE ACTIVES

(75) Inventors: David B. Wurn, Pearland, TX (US); David A. Wilson, Lake Jackson, TX (US); Bruce A. Barner, Sweeny, TX (US); Cynthia L. Rand, Sanford, MI (US); Matthew D. Miller, Lake Jackson, TX (US); Michael J. Johnson, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 369 days.

(21) Appl. No.: 12/810,962

(22) PCT Filed: Jan. 5, 2009

(86) PCT No.: PCT/US2009/030071
§ 371 (c)(1),
(2), (4) Date: Jun. 28, 2010

(87) PCT Pub. No.: WO2009/091622
PCT Pub. Date: Jul. 23, 2009

(65) Prior Publication Data
US 2010/0286277 A1 Nov. 11, 2010

Related U.S. Application Data

(60) Provisional application No. 61/021,935, filed on Jan. 18, 2008.

(51) Int. Cl.
*A61K 9/08* (2006.01)
*A61K 47/10* (2006.01)
*A61K 31/192* (2006.01)
*A61K 31/167* (2006.01)

(52) U.S. Cl.
USPC ............................ 514/570; 514/569; 514/629

(58) Field of Classification Search
USPC ......................................... 514/569, 570, 629
See application file for complete search history.

(56) References Cited

U.S. PATENT DOCUMENTS

| | | |
|---|---|---|
| 3,784,684 A | 1/1974 | Bossert et al. |
| 4,188,376 A | 2/1980 | Payne et al. |
| 4,690,823 A | 9/1987 | Lohner et al. |
| 4,794,117 A | 12/1988 | Corbiere |
| 4,859,704 A | 8/1989 | Haas |
| 4,861,797 A | 8/1989 | Haas |
| 4,944,949 A | 7/1990 | Story et al. |
| 5,004,749 A | 4/1991 | Jerusik et al. |
| 5,071,643 A | 12/1991 | Yu et al. |
| 5,141,961 A | 8/1992 | Coapman |
| 5,200,192 A | 4/1993 | Wimmer |
| 5,431,916 A | 7/1995 | White |
| 5,484,606 A | 1/1996 | Dhabhar |
| 5,910,489 A * | 6/1999 | Falk et al. ............... 514/54 |
| 6,149,930 A | 11/2000 | Bonjour et al. |
| 6,221,391 B1 | 4/2001 | Rouffer |
| 6,251,426 B1 | 6/2001 | Gullapalli |
| 6,551,615 B1 | 4/2003 | Iyer et al. |
| 6,569,439 B1 * | 5/2003 | Stier ..................... 424/401 |
| 6,861,397 B2 | 3/2005 | Seitz, Jr. et al. |
| 2003/0087764 A1 | 5/2003 | Pallas et al. |
| 2005/0201972 A1 | 9/2005 | Seo et al. |
| 2006/0034923 A1 | 2/2006 | Li et al. |
| 2009/0203756 A1 | 8/2009 | Falk et al. |
| 2010/0016390 A1 | 1/2010 | Lenoir et al. |
| 2010/0286217 A1 | 11/2010 | Annis et al. |

FOREIGN PATENT DOCUMENTS

| | | |
|---|---|---|
| DE | 19612085 A1 | 10/1997 |
| EP | 0988789 B1 | 8/2003 |
| GB | 2004747 A | 4/1979 |
| GB | 2397017 B | 6/2005 |
| WO | 9504527 A1 | 2/1995 |
| WO | 9724925 A2 | 7/1997 |
| WO | 9834592 A1 | 8/1998 |
| WO | 0139725 A2 | 6/2001 |
| WO | 0245689 A1 | 6/2002 |
| WO | 03045357 A1 | 6/2003 |
| WO | 2004103342 A2 | 12/2004 |
| WO | 2005102324 A2 | 11/2005 |
| WO | 2006122345 A1 | 11/2006 |
| WO | 2007035515 A2 | 3/2007 |
| WO | 2008013784 A2 | 1/2008 |

OTHER PUBLICATIONS

Emara et al., "Improving the dissolution and bioavailability of nifedipine using solid dispersions and solubilizers", Drug Development and Industrial Pharmacy, 2002, vol. 28 No. 7, pp. 795-807.
International Search Report and Written Opinion for PCT/US2009/030071 dated May 12, 2009.
International Search Report and Written Opinion for PCT/US2007/016597 dated Jan. 21, 2008.
International Search Report and Written Opinion for PCT/US2008/085228 dated Feb. 24, 2009.
CARBOWAX™ and CARBOWAX™ SENTRY™, Polyethylene Glycols and Methoxypolyethylene Glycols, The Dow Chemical Company, Mar. 2006.

* cited by examiner

Primary Examiner — Rachael E Bredefeld

(57) ABSTRACT

A method to enhance solubility of an active compound comprises combining an active compound, having an aqueous solubility that is less than or equal to about 10 mg/mL, and an amount of methoxypolyethylene glycol that is sufficient to increase the aqueous solubility of the active compound. Enhancement of aqueous solubility for this combination may be significantly greater than that of an active compound in combination with an equivalent amount of polyethylene glycol. Particularly enhanced solubility is shown where a small amount of water is also included. The invention may be used in a wide variety of applications, such as for pharmaceutical, agricultural, antimicrobial, and personal care products.

10 Claims, No Drawings

METHOD TO ENHANCE AQUEOUS SOLUBILITY OF POORLY SOLUBLE ACTIVES

CROSS REFERENCE TO RELATED APPLICATIONS

This is a §371 application of PCT International Patent Application Number PCT/US2009/030071 filed Jan. 5, 2009, and claims the benefit of U.S. Provisional Application No. 61/021,935, filed Jan. 18, 2008, each of which is incorporated herein by reference in its entirety.

BACKGROUND OF THE INVENTION

1. Technical Field

The invention relates to improving water solubility of poorly water soluble and insoluble actives. More specifically, it relates to improving the aqueous solubility of a variety of materials produced for the pharmaceutical, agricultural, personal care, and similar industries.

2. Background of the Art

Many of the active compounds used in the pharmaceutical, agricultural, personal care, and similar industries require some degree of dissolution in order to carry out the function for which they are intended. Included among these are, for example, certain analgesics, such as ibuprofen; agricultural compounds, such as ketoconazole; and personal care compounds, such as salicylic acid. This dissolution may be necessary in order to enable the active compound to be useful in a selected environment. This need may create challenges where the active compound is either insoluble in the environment wherein its function is desired, or is only slightly or very slightly soluble therein. In these cases it has been found desirable or necessary to combine the active compound in some way with another material, which serves to enhance its solubility.

A variety of approaches have been pursued to modify solubility of active compounds. As used herein, solubility is defined as the concentration of solute in a saturated solution, and is therefore dependent on factors such as, for example, temperature, solvent, pH of the solution, and pressure. For pharmaceuticals in particular, the solubility of an active compound may be expressed as the number of milliliters of solvent in which one gram of solute (the active compound) will dissolve. For example, in order for a medication to be given orally, the required dose should be able to dissolve in 100-400 mL of water, which is the volume of fluid normally found in the gastrointestinal tract. Because an exact measure of solubility may be difficult to obtain for a given active, solubilities may be generically classified as falling within a given range. These ranges are defined using terms such as "slightly soluble," "sparingly soluble," and the like.

In order to modify solubility of various active compounds, those skilled in the art have generally taken steps such as adjusting the pH, using co-solvents, developing micellar and liposomal systems, forming microemulsions, and employing approaches including complexation, micronization, and nanoization. While each of these approaches has found useful applications, most increase the cost and/or number of steps needed to produce a given product.

For example, U.S. Pat. No. 3,784,684 discloses an oral drug delivery system employing polyethylene glycol (PEG) having a molecular weight of 600 as a component of a solvent system. U.S. Pat. No. 5,071,643 discloses a solvent system containing PEG, water, potassium hydroxide, and polyvinyl pyrrolidone (PVP). WO 95/04527 discloses a solvent system for use in gelatin capsules including PEG, propylene glycol, water, PVP, and potassium or sodium acetate. U.S. Pat. No. 4,690,823 describes a method for preparing ibuprofen-filled soft gel capsules employing ethylene oxide/propylene oxide (EO/PO) block copolymers, surfactant, and/or PEG as part of the solvent system. U.S. Pat. No. 4,859,704 describes enhancing the solubility of ibuprofen in drug formulations by using the salt form of ibuprofen. U.S. Pat. No. 4,861,797 discloses a method for making a palatable ibuprofen composition by dissolving the salt form of the active compound in a solution of water and methylcellulose. U.S. Pat. No. 4,944,949 discloses a drug delivery system employing various nonionic surfactants including PEG fatty acid esters. U.S. Pat. No. 5,141,961 discloses a solvent system using PEG, PVP, and lower alcohols. WO 2003/045357 discloses a formulation for dissolving sparingly water soluble drugs incorporating liquid PEG and derivatized methoxypolyethylene glycol (MPEG) as a surfactant. WO 0139725 describes a wound dressing and transdermal drug delivery system containing MPEG. WO 9834592 discloses a transdermal drug delivery system containing MPEG and methylcellulose for delivery of actives such as non-steroidal anti-inflammatory drugs.

While it will be seen that there are, indeed, a number of ways to enhance the solubility of actives, there are an ever-increasing number of identified actives having their own solubility limitations. Furthermore, ease, convenience and cost of the various known systems are not always optimized. Thus, there is still a need for low cost, effective means to enhance the solubility of certain active compounds in order to enable their use for an intended function.

SUMMARY OF THE INVENTION

Accordingly, the present invention provides, in one aspect, a method of increasing the aqueous solubility of an active compound comprising combining an active compound, having an aqueous solubility that is less than or equal to about 10 mg/mL, and an amount of methoxypolyethylene glycol that is sufficient to increase the aqueous solubility of the active compound.

In another aspect, the invention provides a method of increasing the aqueous solubility of an active compound comprising combining: an active compound, having an aqueous solubility that is less than or equal to about 10 mg/mL; an amount of methoxypolyethylene glycol that is sufficient to increase the aqueous solubility of the active compound; and water; such that the ratio of methoxypolyethylene glycol: water, based on weight percent, is from about 70:30 to about 99:1.

In yet another aspect, the invention provides a composition comprising an active compound having an aqueous solubility of less than or equal to about 10 mg/mL, and an amount of methoxypolyethylene glycol that is sufficient to increase the aqueous solubility of the active compound.

DETAILED DESCRIPTION OF THE EMBODIMENTS

It has been found that inclusion of methoxypolyethylene glycol (MPEG) with an active compound may serve to increase the solubility of the active compound in environments to which the active compound is to be exposed. Such environments may include environments comprising or consisting of water, alcohol, or combinations thereof. Such may further include biological environments such as those experienced during human or animal ingestion and digestion, for example, for pharmaceutical applications; agricultural environments; combinations thereof; and the like.

The invention employs MPEG in any amount sufficient to increase or enhance the aqueous solubility of the active compound, beyond what it would be in the absence of the MPEG. Such amount is termed herein as an "effective amount." The "active compound" is herein defined as any compound being employed to produce a desirable, and measurable, effect in the environment for which it is targeted, and which has an aqueous solubility that is, at most, about 10 mg/mL, i.e., that falls within the definition of "slightly soluble," "very slightly soluble," or "insoluble," according to Table 1 hereinbelow.

TABLE 1*

| Term | Parts of Solvent Required for 1 Part of Solute | Solubility defined in mg/mL |
| --- | --- | --- |
| Very Soluble | Less than 1 part | >1,000 mg/mL |
| Freely Soluble | 1 to 10 parts | 100-1,000 mg/mL |
| Soluble | 10 to 30 parts | 33-100 mg/mL |
| Sparingly Soluble | 30 to 100 parts | 10-33 mg/mL |
| Slightly Soluble | 100 to 1,000 parts | 1-10 mg/mL |
| Very Slightly Soluble | 1,000 to 10,000 parts | 0.1-1 mg/mL |
| Insoluble | >10,000 parts | <0.1 mg/mL |

*Taken from "Delivery of Poorly Soluble or Poorly Permeable Drugs," Fifth Edition (Technology Catalysts International, publ., December 2004)

As will be obvious, there is a small overlap at the outer limits of each category, but this table is generally useful for defining the solution behavior of a wide variety of active compounds, termed in the table as the "solute," while limiting the selection of "solvent," as used therein, to water. Examples may include pharmaceuticals, such as naproxen and ibuprofen, which will be ingested by a human or animal subject. Other medicinal and veterinary products may also benefit from the effect of the MPEG, as well as agricultural products such as biocides, herbicides, plant growth enhancers, and the like. Personal care and other products, including, for example, cosmetics, cleansers, and antimicrobials, may also benefit from practice of the invention.

The MPEG used herein may function as an adjuvant, thereby serving only to modify the aqueous solubility of the active compound while remaining otherwise essentially inactive in many formulations. It may be used in essentially any molecular weight, according to the needs of the active compound. For practical purposes, however, MPEG is most conveniently available as a commercial product, and a molecular weight ranging from about 100 to about 1,000 fulfills the needs of many applications. It is noted, however, that pharmaceutical applications, in particular, may proscribe use of very low molecular weight forms. In such cases, as well as in some other non-limiting embodiments, MPEG having a molecular weight ranging from about 350 to about 1,000 may be preferred. A 350 mw version, such as CARBOWAX™ Methoxypolyethylene Glycol 350, available from The Dow Chemical Company, offers relatively inexpensive but very effective solubility enhancement. Enhancement of aqueous solubility may be obtained by practice of the invention whether the MPEG is in solid or liquid form under ambient conditions, but for many non-limiting embodiments, liquid forms having a relatively low molecular weight within the defined ranges may be preferred. Those skilled in the art will be easily able to identify commercial sources of MPEG or, alternatively, will be able to prepare MPEG by methods well publicized in the art or which may be devised upon routine experimentation. For example, one known and convenient method involves ethoxylation of methanol by basic catalysis.

The MPEG may be combined in formulations with other modifiers, in order to enable a wide variety of possibilities for any given active compound. For example, in some non-limiting embodiments, it may be combined in formulations of active compounds with surfactants, including but not limited to nonionic surfactants, such as ethoxylated castor oil, alkoxylated triglycerides, combinations thereof, and the like. In other non-limiting embodiments, it may also be combined with other solubility enhancers, such as, for example, polyethylene glycol (PEG); polyvinyl pyrrolidone (PVP); block or random copolymers of ethylene oxide, propylene oxide, butylene oxide, and combinations of any of these; combinations thereof; and the like. In yet other non-limiting embodiments, it may also be combined with viscosity modifiers, gelling agents, pigments, colorants, lubricants, foaming agents, combinations thereof, and the like. Thus, the use of MPEG as a solubility enhancer may be employed in a wide variety of applications.

In incorporating the MPEG with the selected active compound, it is generally not necessary to employ an increased temperature. Ambient conditions of temperature and pressure are, in many non-limiting embodiments, adequate to enable suitable dissolution of the active compound in the MPEG, with or without an additional solvent such as water, alcohol, or a combination thereof. It should be understood that, while the invention addresses those active compounds that are defined by their limited solubility in water, the invention does not require that water per se be used in preparing the product that will consist of or contain the active compound. For example, where the formulation is destined for ultimate use as a gel or liquid, the MPEG may serve as the primary solvent, along with, in some non-limiting embodiments, one or more secondary solvents, such as water, alcohol, or a combination thereof. This is because one particular advantage of using MPEG is that, at molecular weights below about 750, it is generally in the form of a clear, relatively low viscosity liquid, and at molecular weights above about 750, it is in the form of a white solid of paste-like consistency. In either form, it may be incorporated into a variety of formulations with active compounds, which may then be used to prepare, for example, gels, soft gels, capsules, tablets, granules, liquids, foams, and the like.

A particular synergism between water and MPEG does exist, however, in certain non-limiting embodiments, and in such embodiments a ratio of MPEG:water, based on weight percent, of from about 70:30 to about 99:1 may be particularly useful. In other non-limiting embodiments, the ratio may be from about 80:20 to about 98:2, and in still other non-limiting embodiments, it may be from about 85:15 to about 97:3. In one particular embodiment, a ratio of about 95:5 may be employed. On a mole basis, a ratio of MPEG:water, in some non-limiting embodiments, of from about 0.8:1 to about 1.2:1 may be used. In other non-limiting embodiments, a molar ratio of from about 0.9:1 to about 1.1 may be used, and in still another non-limiting embodiment, a molar ratio of about 1:1 may be selected. This synergism may exhibit itself as particularly enhanced solubility of a given included active compound included in the formulation.

Formulations including MPEG may also exhibit significant stability, alternatively referred to as shelf-life. MPEG is not significantly volatile, which means that the concentration of the active compound in a given formulation will remain approximately the same for a significant period of time. This may be particularly important in pharmaceutical applications, where dosage consistency is highly desirable. Furthermore, with MPEG the enhancement of solubility is not obtained by making the active compound subject to hydrolysis, and thus, the essential chemistry of the active compound is preserved. Where an active compound is acidic in nature, MPEG is also less likely to result in esterification of the active compound than, for example, may occur where an equivalent amount of PEG is employed for the same purpose. Finally, as already noted hereinabove, MPEG may be included in many formulations without any application of heat, thereby avoiding degradation of either an active compound or of the MPEG itself.

The description hereinabove is intended to be general and is not intended to be inclusive of all possible embodiments of the invention. Similarly, the examples hereinbelow are provided to be illustrative only and are not intended to define or limit the invention in any way. Those skilled in the art will be fully aware that other embodiments within the scope of the claims will be apparent, from consideration of the specification and/or practice of the invention as disclosed herein. Such other embodiments may include selections of specific active compounds and specific molecular weight range MPEG products; identification and proportions of starting and resulting compounds at each process step; mixing and other formulation conditions, vessels, and protocols; performance and selectivity; applications of the final products; and the like. Those skilled in the art will recognize that such may be varied within the scope of the claims appended hereto.

EXAMPLES

Example 1 (Comparative)

A solution of ibuprofen is prepared by dissolving approximately 1.79 g of ibuprofen in about 4.8 g of MPEG 350 at room temperature (about 20° C.). The solution is then stirred with a vortex mixer for approximately 1 to 2 minutes, then shaken with an automated shaker for about 45 minutes. The sample is clear. The sample is then left overnight in a water bath at about 29° C. The 27.2 weight percent solution is observed to be clear. Maximum ibuprofen loading at room temperature is quantified using high performance liquid chromatography (HPLC) and found to be about 26.8±0.5 weight percent.

For comparison, approximately 1.58 g of ibuprofen is dissolved in about 4.23 g of PEG 400 in an identical manner to that described in this Example 1, resulting in a saturated solution. The solubility (maximum loading) of ibuprofen in PEG 400 is found to be 21.6±0.8 weight percent by HPLC. The amount of drug loading for the MPEG 350 ibuprofen solution is, therefore, approximately 24 percent higher than for the PEG 400 ibuprofen solution. Table 2 shows the results.

Example 2 (Comparative)

A solution of naproxen is prepared by dissolving about 0.8929 g of naproxen in about 4.91 g of MPEG 350 at room temperature (about 19 to 20° C.). The solution is stirred with a vortex mixer for approximately 1 to 2 minutes, then shaken with an automated shaker for about 45 minutes. A milky suspension is observed at this point. The sample is left overnight in a water bath at about 30° C. The approximately 15.4 weight percent solution is observed to have some suspended material. The maximum loading is determined by HPLC to be about 14.2±0.3 weight percent.

For comparison, approximately 0.8804 g of naproxen is dissolved in about 4.82 g of PEG 400 in an identical manner to that described hereinabove, resulting in a saturated solution. The nominal concentration of this solution is about 15.5 weight percent. The maximum loading of naproxen in this system is determined to be about 12.5±0.4 weight percent by HPLC. The amount of naproxen dissolved in the MPEG 350 solution is approximately 13.6 percent greater than the amount dissolved in the PEG 400 solution. Table 2 shows the results.

Example 3 (Comparative)

Solutions of ibuprofen are made by dissolving the ibuprofen in a mixture of MPEG 350 and water until saturation is reached. The solutions are then filtered through a syringe filter and the concentrations are characterized by HPLC. The percent water in the MPEG solutions varies from 0 to 20 percent. The highest loading is achieved for a 5 percent water, 95 percent MPEG 350 solution, and is determined to be approximately 30.7 weight percent. This is a 14.6 percent increase in loading when compared to the MPEG 350 solution containing no water.

For comparison, solutions of PEG 400 and water are prepared in an analogous manner to those including the MPEG 350. Ibuprofen is dissolved in these solutions and filtered in the same manner as above. The maximum loading achieved for any of the PEG 400:water binary blends is 24.3 weight percent. Therefore, 26.3 weight percent more loading is achieved with the 95:5 MPEG 350:water blend, compared to the PEG 400:water blends having the highest loading. Table 2 shows the results.

Example 4 (Comparative)

Solutions of naproxen are made by dissolving the naproxen in a mixture of MPEG 350 and water until saturation is reached. The solution is then filtered through a syringe filter and the concentration is characterized by HPLC. The percent water in the MPEG solutions varies from 0 to 20 percent. The highest loading is achieved in a solution of 95 percent MPEG 350, 5 percent water, and is determined to be approximately 17.7 weight percent. This is a 24.4 percent increase in loading compared to the MPEG 350 solution containing no water.

For comparison, solutions of PEG 400 and water are prepared in an analogous manner. Naproxen is dissolved in these solutions and filtered in the same manner as described hereinabove. The maximum ("best") naproxen loading achieved for any of the PEG 400: water binary blends is approximately 13.7 weight percent. Therefore, 29.2 weight percent more loading is achieved with the 95:5 MPEG 350:water blend compared to the "best" PEG 400: water blend. Table 2 shows the results.

Example 5 (Comparative)

Acetaminophen is dissolved in MPEG 350: water and PEG 400: water blends and then characterized by methods identical to those described in Example 3 (Comparative) and Example 4 (Comparative). For acetaminophen, the PEG 400 neat solution solubilizes slightly more acetaminophen than does the neat MPEG 350 solution. When water is added, higher loading is obtained with the MPEG:water blends than with the PEG:water blends. The maximum solubility for the MPEG 350: water blends is 10.6 percent greater than that obtained for the PEG 400: water blends. The testing results that illustrate the MPEG 350: water synergism are shown in Table 2.

TABLE 2

| Percent water | Percent Loading Using MPEG 350 | Standard Deviation | Percent Loading Using PEG 400 | Standard Deviation |
|---|---|---|---|---|
| Acetaminophen | | | | |
| 0 | 16.20 | 0.08 | 16.82 | 0.08 |
| 5 | 21.93 | 0.16 | 20.62 | 0.06 |
| 10 | 23.62 | 0.06 | 21.78 | 0.07 |
| 15 | 24.47 | 0.11 | 22.12 | 0.20 |
| 20 | 24.01 | 0.19 | 21.59 | 0.11 |
| Ibuprofen | | | | |
| 0 | 26.80 | 0.53 | 21.60 | 0.80 |
| 5 | 30.70 | 0.46 | 24.31 | 1.37 |
| 10 | 29.77 | 0.51 | 21.48 | 0.09 |
| 15 | 27.35 | 0.71 | 17.24 | 0.03 |
| 20 | 23.09 | 0.1 | 11.56 | 0.03 |
| Naproxen | | | | |
| 0 | 14.22 | 0.29 | 12.48 | 0.41 |
| 5 | 17.69 | 0.11 | 13.65 | 0.11 |
| 10 | 16.91 | 0.11 | 12.97 | 0.38 |
| 15 | 14.68 | 0.15 | 10.21 | 0.03 |

What is claimed is:

1. A method of increasing the aqueous solubility of an active compound comprising combining an active compound having an aqueous solubility that is less than or equal to about 10 mg/mL selected from the group consisting of acetaminophen, ibuprofen, naproxen, and combinations thereof, an amount of methoxypolyethylene glycol sufficient to increase the aqueous solubility of the active compound, and water, such that the ratio of methoxypolyethylene glycol:water, based on weight percent, is from about 80:20 to about 90:10.

2. The method of claim 1 further comprising combining an alcohol with the active compound, methoxypolyethylene glycol, and water.

3. The method of claim 1 wherein the methoxypolyethylene glycol has a molecular weight of from about 100 to about 1,000.

4. The method of claim 1 further comprising combining a nonionic surfactant selected from the group consisting of ethoxylated castor oil, alkoxylated triglycerides, and combinations thereof with the active compound, methoxypolyethylene glycol, and water.

5. The method of claim 1 further comprising combining polyethylene glycol (PEG); polyvinylpyrrolidone (PVP); block or random copolymers of ethylene oxide and propylene oxide; or combinations thereof with the active compound, methoxypolyethylene glycol, and water.

6. The method of claim 1 wherein the active compound, methoxypolyethylene glycol, and water are comprised in a formulation having a pharmaceutical, agricultural, antimicrobial, or personal care use.

7. The method of claim 6 further comprising processing the formulation to form a product selected from the group consisting of gels, soft gels, tablets, capsules, liquids, foams, and granules.

8. A composition comprising an active compound having an aqueous solubility of less than or equal to about 10 mg/mL selected from the group consisting of acetaminophen, ibuprofen, naproxen, and combinations thereof, an amount of methoxypolyethylene glycol that is sufficient to increase the aqueous solubility of the active compound, and water in an amount such that the ratio of methoxypolyethylene glycol:water, based on weight percent, is from about 80:20 to about 90:10.

9. The composition of claim 8 wherein the methoxypolyethylene glycol has a molecular weight ranging from about 100 to about 1000.

10. The composition of claim 9 wherein the methoxypolyethylene glycol has a molecular weight of about 350.

* * * * *

UNITED STATES PATENT AND TRADEMARK OFFICE
CERTIFICATE OF CORRECTION

| | | |
|---|---|---|
| PATENT NO. | : 8,497,303 B2 | Page 1 of 1 |
| APPLICATION NO. | : 12/810962 | |
| DATED | : July 30, 2013 | |
| INVENTOR(S) | : David B. Wurm et al. | |

It is certified that error appears in the above-identified patent and that said Letters Patent is hereby corrected as shown below:

On the title page, item (75) Inventors of the above identified patent incorrectly lists an inventors name. The correct name should be David B. WURM.

Signed and Sealed this
Eighteenth Day of February, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,497,303 B2 | Page 1 of 1 |
| APPLICATION NO. | : 12/810962 | |
| DATED | : July 30, 2013 | |
| INVENTOR(S) | : David B. Wurm et al. | |

It is certified that error appears in the above-identified patent and that said Letters Patent is hereby corrected as shown below:

On the title page, item (12), delete "Wurn" and insert --Wurm--.

On the title page, item (75) Inventors of the above identified patent incorrectly lists an inventors name. The correct name should be David B. WURM.

This certificate supersedes the Certificate of Correction issued February 18, 2014.

Signed and Sealed this
Twenty-fifth Day of March, 2014

Michelle K. Lee
*Deputy Director of the United States Patent and Trademark Office*